United States Patent
Gliner et al.

(10) Patent No.: US 6,959,215 B2
(45) Date of Patent: Oct. 25, 2005

(54) METHODS FOR TREATING ESSENTIAL TREMOR

(75) Inventors: Bradford Evan Gliner, Sammamish, WA (US); Allen Wyler, Seattle, WA (US)

(73) Assignee: Northstar Neuroscience, Inc., Seattle, WA (US)

( * ) Notice: Subject to any disclaimer, the term of this patent is extended or adjusted under 35 U.S.C. 154(b) by 0 days.

(21) Appl. No.: 10/622,898

(22) Filed: Jul. 17, 2003

(65) Prior Publication Data

US 2004/0111129 A1 Jun. 10, 2004

Related U.S. Application Data

(60) Provisional application No. 60/432,073, filed on Dec. 9, 2002.

(51) Int. Cl.⁷ ............................................. A61N 1/36
(52) U.S. Cl. ............................................ 607/45; 607/48
(58) Field of Search ................................. 607/45, 48

(56) References Cited

U.S. PATENT DOCUMENTS

| | | | |
|---|---|---|---|
| 3,650,276 A | 3/1972 | Burghele et al. ............ | 607/27 |
| 4,140,133 A | 2/1979 | Kastrubin et al. ............ | 607/46 |
| 4,431,000 A | 2/1984 | Butler et al. ................. | 607/73 |
| 4,542,752 A | 9/1985 | DeHaan ....................... | 607/119 |
| 4,607,639 A | 8/1986 | Tanagho ...................... | 607/40 |

(Continued)

FOREIGN PATENT DOCUMENTS

| | | | | |
|---|---|---|---|---|
| EP | 0 998 958 A2 | * | 5/2000 | ............ A61N/1/36 |
| EP | 0 998 958 A | | 10/2000 | ............ A61N/1/36 |
| EP | 1 145 736 | | 10/2001 | |
| WO | WO 87/07511 | | 12/1987 | ............ A61N/1/36 |
| WO | WO 94/07564 | | 4/1994 | ............ A61N/1/04 |

(Continued)

OTHER PUBLICATIONS

Bel, S. and Bauer, B.L., "Dorsal Column Stimulation (DCS): Cost to Benefit Analysis," Acta Neurochirurgica, Suppl. 52, pp. 121–123 (1991).

Benabid, A.L. et al, "Chronic electrical stimulation of the ventralis intermedius nucleus of the thalamus as a treatment of movement disorders," J. Neurosurg., Apr. 1997, 86(4); 737; http://www.ncbi.nlm.nih.gov; [accessed Nov. 18, 2003].

Butefisch et al., "Mechanisms of use–dependent plasticity in the human motor cortex," Proc. Natl. Acad. Sci. USA, vol. 97, No. 7, pp. 3661–3665 (Mar. 2000).

Canavero, S. and Paolotti, R., "Extradural Motor Cortex Stimulation afor Advanced Parkinson's Disease: Case Report," Movement Disorders, 15(1):169–171,2000.

Cincotta et al., "Reorganization of the motor cortex in a patient with congenital hemiparesis and mirror movements," Neurology, vol. 55, pp. 129–131 (2000).

(Continued)

*Primary Examiner*—Carl Layno
(74) *Attorney, Agent, or Firm*—Perkins Coie LLP

(57) ABSTRACT

A method for treating essential tremor includes directing a patient to perform a muscle action, for example a postural or kinetic muscle action. The method can further include collecting information, with the information corresponding to a level of neural activity in the patient's brain while the patient performs the muscle action. The essential tremor motion of the patient can then be at least reduced by applying an electrical stimulation at least proximate to a stimulation site, with the location of the stimulation site being based at least in part on the collected information. The information can include visual images (e.g. MRI, fMRI, or CT techniques) or be non-visual. In particular embodiments, the location of the stimulation site can be determined by comparing two pieces of information, for example, neural activities before and after drug intake, or neural activities at the left and right hemispheres of the brain.

43 Claims, 9 Drawing Sheets

U.S. PATENT DOCUMENTS

| | | | |
|---|---|---|---|
| 4,646,744 A | 3/1987 | Capel | 607/58 |
| 4,844,075 A | 7/1989 | Liss | 607/45 |
| 4,865,048 A | 9/1989 | Eckerson | 607/45 |
| 5,002,053 A | 3/1991 | Garcia-Rill | 607/49 |
| 5,031,618 A | 7/1991 | Mullett | 607/46 |
| 5,054,906 A | 10/1991 | Lyons | 351/205 |
| 5,092,835 A | 3/1992 | Schurig | 600/9 |
| 5,143,089 A | 9/1992 | Alt | 607/121 |
| 5,169,384 A | 12/1992 | Bosniak | 604/20 |
| 5,215,086 A | 6/1993 | Terry | 607/46 |
| 5,224,491 A | 7/1993 | Mehra | 607/126 |
| 5,255,678 A | 10/1993 | Deslauriers | 600/375 |
| 5,263,967 A | 11/1993 | Lyons | 606/205 |
| 5,304,206 A | 4/1994 | Baker | 607/2 |
| 5,314,458 A | 5/1994 | Najafi et al. | 607/116 |
| 5,358,513 A | 10/1994 | Powell | 607/48 |
| 5,370,672 A | 12/1994 | Fowler | 607/58 |
| 5,411,540 A | 5/1995 | Edell | 607/53 |
| 5,417,719 A | 5/1995 | Hull | 607/46 |
| 5,423,864 A | 6/1995 | Ljungstroem | 607/5 |
| 5,537,512 A | 7/1996 | Hsia | 706/39 |
| 5,540,736 A | 7/1996 | Haimovich | 607/46 |
| 5,549,655 A | 8/1996 | Erickson | 607/42 |
| 5,575,813 A | 11/1996 | Edell | 607/116 |
| 5,591,216 A | 1/1997 | Testerman | 607/42 |
| 5,593,432 A | 1/1997 | Crowther et al. | 607/46 |
| 5,628,317 A | 5/1997 | Starkebaum | 600/437 |
| 5,683,422 A | 11/1997 | Rise | 607/2 |
| 5,702,429 A | 12/1997 | King | 607/46 |
| 5,711,316 A | 1/1998 | Elsberry | 128/898 |
| 5,713,922 A | 2/1998 | King | 607/2 |
| 5,713,923 A | 2/1998 | Ward | 607/3 |
| 5,716,377 A | 2/1998 | Rise | 607/2 |
| 5,722,401 A | 3/1998 | Pietroski | 600/374 |
| 5,735,814 A | 4/1998 | Elsberry | 604/43 |
| 5,752,979 A | 5/1998 | Benabid | 607/72 |
| 5,782,798 A | 7/1998 | Rise | 604/500 |
| 5,792,186 A | 8/1998 | Rise | 607/2 |
| 5,797,970 A | 8/1998 | Pouvreau | 607/9 |
| 5,814,014 A | 9/1998 | Elsberry | 604/43 |
| 5,814,092 A | 9/1998 | King | 607/46 |
| 5,824,021 A | 10/1998 | Rise | 607/46 |
| 5,832,932 A | 11/1998 | Elsberry | 128/898 |
| 5,833,709 A | 11/1998 | Rise | 607/2 |
| 5,843,148 A | 12/1998 | Gijsbers | 607/116 |
| 5,843,150 A | 12/1998 | Dreessen | 607/116 |
| 5,885,976 A | 3/1999 | Sandyk | 514/159 |
| 5,886,769 A | 3/1999 | Zolten | 351/219 |
| 5,893,883 A | 4/1999 | Torgerson | 607/59 |
| 5,904,916 A | 5/1999 | Hirsch | 424/45 |
| 5,913,882 A | 6/1999 | King | 607/62 |
| 5,925,070 A | 7/1999 | King | 607/67 |
| 5,938,688 A | 8/1999 | Schiff | 607/45 |
| 5,938,689 A | 8/1999 | Fischell | 607/45 |
| 5,941,906 A | 8/1999 | Barreras | 607/66 |
| 5,964,794 A | 10/1999 | Bolz | 607/121 |
| 5,975,085 A | 11/1999 | Rise | 128/898 |
| 5,978,702 A | 11/1999 | Ward | 607/3 |
| 5,983,140 A | 11/1999 | Smith | 607/59 |
| 6,006,124 A | 12/1999 | Fischell | 600/378 |
| 6,011,996 A | 1/2000 | Gielen | 607/116 |
| 6,016,449 A | 1/2000 | Fischell | 607/45 |
| 6,018,682 A | 1/2000 | Rise | 607/45 |
| 6,021,352 A | 2/2000 | Christopherson | 607/42 |
| 6,026,326 A | 2/2000 | Bardy | 607/40 |
| 6,042,579 A | 3/2000 | Elsberry | 604/891.1 |
| 6,052,624 A | 4/2000 | Mann | 607/46 |
| 6,055,456 A | 4/2000 | Gerber | 607/117 |
| 6,057,847 A | 5/2000 | Jenkins | 345/422 |
| 6,058,331 A | 5/2000 | King | 607/62 |
| 6,060,048 A | 5/2000 | Cherksey | 424/93.1 |
| 6,061,593 A | 5/2000 | Fischell | 600/544 |
| 6,066,163 A | 5/2000 | John | 607/45 |
| 6,104,956 A | 8/2000 | Naritoku | 607/45 |
| 6,104,960 A | 8/2000 | Duysens et al. | 607/117 |
| 6,122,548 A | 9/2000 | Starkebaum et al. | 607/67 |
| 6,126,657 A | 10/2000 | Edwards et al. | 606/45 |
| 6,128,537 A | 10/2000 | Rise | 607/45 |
| 6,128,538 A | 10/2000 | Fischell et al. | 607/45 |
| 6,134,474 A | 10/2000 | Fischell et al. | 607/45 |
| 6,152,143 A | 11/2000 | Edwards | 128/898 |
| 6,161,044 A * | 12/2000 | Silverstone | 607/45 |
| 6,161,045 A | 12/2000 | Fischell et al. | 607/45 |
| 6,221,908 B1 | 4/2001 | Kilgard et al. | 514/546 |
| 6,353,754 B1 | 3/2002 | Fischell et al. | 600/544 |
| 6,354,299 B1 | 3/2002 | Fischell et al. | 128/899 |
| 6,360,122 B1 | 3/2002 | Fischell et al. | 600/544 |
| 6,366,813 B1 * | 4/2002 | DiLorenzo | 607/45 |
| 6,405,079 B1 | 6/2002 | Ansarinia | 607/2 |
| 6,418,344 B1 | 7/2002 | Rezai et al. | 607/45 |
| 6,427,086 B1 | 7/2002 | Fischell et al. | 607/45 |
| 6,459,936 B2 | 10/2002 | Fischell | 607/45 |
| 6,463,328 B1 * | 10/2002 | John | 607/45 |
| 6,466,822 B1 | 10/2002 | Pless | 455/1 |
| 6,473,639 B1 | 10/2002 | Fischell | 600/544 |
| 6,480,743 B1 | 11/2002 | Kirkpatrick | 607/45 |
| 6,499,488 B1 | 12/2002 | Hunter et al. | 128/899 |
| 6,622,048 B1 | 9/2003 | Mann | 607/46 |
| 6,687,525 B2 | 2/2004 | Llinas et al. | 600/407 |
| 6,690,974 B2 | 2/2004 | Archer et al. | 607/45 |
| 6,795,737 B2 | 9/2004 | King | 607/117 |
| 2002/0028072 A1 | 3/2002 | Kashiyama | 396/106 |
| 2002/0055675 A1 | 5/2002 | Llinas | 600/407 |
| 2002/0077670 A1 | 6/2002 | Archer | 607/45 |
| 2002/0087201 A1 | 7/2002 | Firlik | 607/45 |
| 2002/0091419 A1 * | 7/2002 | Firlik et al. | 607/45 |
| 2002/0099412 A1 | 7/2002 | Fischell | 607/3 |
| 2002/0161415 A1 * | 10/2002 | Cohen et al. | 607/48 |
| 2002/0169485 A1 | 11/2002 | Pless | 607/48 |
| 2003/0149457 A1 * | 8/2003 | Tcheng et al. | 607/48 |
| 2003/0187490 A1 | 10/2003 | Gliner | 607/116 |
| 2004/0158298 A1 | 8/2004 | Gliner | 607/48 |

FOREIGN PATENT DOCUMENTS

| | | | |
|---|---|---|---|
| WO | WO 95/21591 | 8/1995 | A61F/2/02 |
| WO | WO 98/06342 | 2/1998 | A61B/17/52 |
| WO | WO 01/97906 | 12/2001 | A61N/1/36 |
| WO | WO 02/09811 | 2/2002 | A61N/2/02 |
| WO | WO 02/36003 | 5/2002 | A61B/5/0484 |
| WO | WO 02/38031 | 5/2002 | A61B/5/04 |
| WO | WO 02/38217 | 5/2002 | A61N/1/36 |
| WO | WO 03/082402 | 3/2003 | A61N/1/36 |
| WO | WO 03/043690 | 5/2003 | A61N/1/36 |

OTHER PUBLICATIONS

Classen, et al., "Rapid Plasticity of Human Cortical Movement Representation Induced by Practice," The Journal of Neurophysiology, vol. 79, No. 2, pp. 1117–1123 (Feb. 1998).

Cohen et al., "Studies of Neuroplasticity With Transcranial Magnetic Stimulation," The Journal of Clinical Neurophysiology, vol. 15, No. 4 (1998).

Cramer, S.C. and Bastings, E.P., "Mapping clinically relevant plasticity after stroke," Neuropharmacology vol. 19, No. 5, pp. 842–851 (Apr. 2000).

Dam et al., "Effects of Fluoxetine and Maprotiline on Functional Recovery in Poststroke Hemiplegic Patients Undergoing Rehabilitation Therapy," Stroke, vol. 27, No. 7, pp. 1211–1214 (Jul. 1996).

Feys et al., "Value of somatosensory and motor evoked potentials in predicting arm recovery after a stroke," (Oct. 1999).

Franzini et al., "Reversal of thalamic hand syndrome by long–term motor cortex stimulation," Journal of Neurosurgery 93:873–875 (2000).

Gladstone et al., "Enhancing Recovery after Stroke with Noradrenergic Pharmacotherapy: A New Frontier?," Can J. Neurol. Sci., vol. 27, No. 2 (May 2000).

Gordon et al., "Parameters for direct cortical electrical stimulation in the human: histopathologic confirmation," Electroencephalography and clinical Neurophysiology, vol. 75, pp. 371–377 (1990).

Hodge, Jr., C.J. and Boakye, M., "Biological Plasticity: The Future of Science in Neurosurgery," Neurosurgery, vol. 48, No. 1 (Jan. 2001).

International Search Report for Application No. PCT/US02/07077; Applicant: Vertis Neuroscience, Inc., Oct. 22, 2002, 7 pgs.

International Search Report for Application No. PCT/US02/32695; Applicant: Vertis Neuroscience, Inc.; Dec. 27, 2002; 9 pgs.; European Patent Office.

Kauhanen et al., "Domans and Determinants of Quality of Life After Stroke Caused by Brian Infarction," Arch. Phys., Med. Rehabil., vol. 81, pp. 1541–1546 (Dec. 2000).

Kopell et al., "The Continuing Evolution of Psychiatric Neurosurgery," CNS Spectrums, vol. 5, No. 10, pp. 20–31 (Oct. 2000).

Levy et al., "Functional MRI Evidence of Cortical Reorganization in Upper–Limb Stroke Hemiplegia Treated with Constraint–Induced Movement Therapy," American Journal of Physical Medicine & Rehabilitation, vol. 80, No. 1, pp. 4–7 (2001).

Liepert et al., "Treatment–Induced Cortical Reorganization After Stroke in Humans," Stroke, 31:1210–1216 (2000).

Malenka, R.C. and Nicoll, R.A., "Long–Term Potenetiation—A Decade of Progress?," Neuroscience, vol. 285, No. 5435, Issue of Sep. 17, 1999, pp. 1870–1874.

Martinez et al., "Motor hand recovery after stroke Prognostic yield of early transcranial magnetic stimulation," Electromyography. Clin. Neurophysiology, vol. 39, pp. 405–410 (1999).

Netz et al., "Reorganization of motor output in the non–affected hemisphere after stroke," Brain, 120, pp. 1579–1586 (1997).

Nitsche, M.A. and Paulus, W., "Excitability changes induced in the human motor cortex by weak transcranial direct current stimulation," The Journal of Physiology, vol. 527.3, pp. 663–639 (2000).

Oliveri et al., "Paired transcranial magnetic stimulation protocols reveal a pattern of inhibition and facilitation in the human parietal cortex," The Journal of Physiology, 529.2, pp. 461–468 (2000).

Pascual–Leone et al., "Study and Modulation of Human Cortical Excitability With Transcranial Magnetic Stimulation," Journal of Clinical Neurophysiology, vol. 15, No. 4 (1998).

Pascual–Leone et al., "Transcranial magnetic stimulation and neuroplasticity," Neurophycologia 37, pp. 207–217 (1999).

Rezai, "Neurostimulation," Neurological Research, vol. 22, No. 3 pp. 235–273 (Apr. 2000).

Rossi et al., "Effects of Repetitive Transcranial Magnetic Stimulation on Movement–related Cortical Activity in Humans," Cerebral Cortex, vol. 10, No. 8, pp. 802–808 (Aug. 2000).

Roux et al., "Chronic Motor Cortex Stimulation for Phantom Limb Pain: A Functional Magnetic Resonance Imagining Study: Technical Cast Report," Neurosurgery, vol. 49, No. 3 (Mar. 2001).

Saitou et al., "Cerebral Blood.Volume and Oxygenation Among Poststroke Hemiplegic Patients: Effects of 13 Rehabilitation Tasks Measured by Near–Infrared Spectroscopy," Arch. Phys. Med. Rehabil., vol. 81 pp. 1348–1356 (Oct. 2000).

Sandkuhler, "Learning and memory in pain pathways," Pain 88, pp. 113–118 (2000).

Sanes, "The Relation between Human Brain Activity and Hand Movements," NeuroImage 11, pp. 370–374 (2000).

Sanes, J. and Donoghue, J.P., "Plasticity and Primary Motor Cortex," Annual Review of Neuroscience 23:393–415 (2000).

Sanes, J.N. and Donoghue, J.P., "Plasticity and Primary Motor Cortex," Annu. Rev. Neurosci. 23:393–415 (2000).

Schiff et al., "A neuromodulation strategy for rational therapy of complex brain injury states," Neurological Research, vol. 22 pp. 267–272 (Apr. 2000).

Shimizu et al., "Therapeutic efficacy of transcranial magnetic stimulation for hereditary spinocerebellar degeneration," Tohoku Journal of Experimental Medicine, 189(3):203–11 (Nov. 1999).

Siebner et al., "Lasting cortical activation after repetitive TMS of the motor cortex," Neurology 54, ###pp. 956–963 (Feb. 2000)###.

Stefan et al., "Induction of plasticity in the human motor cortex by paired associative stimulation," Brain, 123, pp. 572–584 (2000).

Stefan et al., "Introduction of plasticity in the human motor cortex by paired associative stimulation," Brian, vol. 123, No. 3, pp. 575–584 (Mar. 2000).

Turton et al., "Contralateral and ipsilateral EMG responses to transcranial magnetic stimulation during recovery of arm and hand function after stroke," Electroencephalography and Clinical Neurophysiology 101 pp. 316–328 (1996).

Turton, A. and Lemon, R.N., "The contribution of fast corticospinal input to the voluntary activation of proximal muscles in normal subjects and in stroke patients," Exp. Brain Res., vol. 129, pp. 559–572 (1999).

Van Der Lee et al., "The Intra– and Interrater Reliability of the Action Research Arm Test: A Practical Test of Upper Extremity Function in Patients With Stroke," Arch. Phys. Med. Rehabil., vol. 82 pp. 14–19 (Jan. 2001).

Walker–Batson et al., "Amphetamine Paired With Physical Therapy Accelerates Motor Recovery After Stroke," Stroke, vol. 26, No. 12, pp. 2254–2259 (1995).

Ziemann et al., "Modulation of Plasticity in Human Motor Cortex after Forearm Ischemic Nerve Block," The Journal of Neuroscience 18(3):1115–1123 (Feb. 1998).

Ziemann et al., "Modulation of Plasticity in Human Motor Cortex after Forearm Ischemic Nerve Block," The Journal of Neuroscience, vol. 18, No. 3, pp. 1115–1123 (Feb. 1998).

International Search Report for PCT/US03/39077; May 2004; Applicant: Northstar Neuroscience, Inc. (3 pgs).

International Search Report for PCT/US03/03678; Jul.; 2003: Applicant: Northstar Neuroscience, Inc. (4 pgs).

International Search Report for PCT/US03/39078; May 2004; Applicant: Northstar Neuroscience, Inc.

International Search Report for PCT/US02/31112; Dec. 2002; Applicant: Vertis Neuroscience, Inc. (3 pgs).

International Search Report for PCT/US02/31127; Jul. 2003; Applicant: Vertis Neuroscience, Inc. (3 pgs).

International Search Report for PCT/US02/31128; Sep. 2002; Applicant: Vertis Neuroscience, Inc. (3 pgs).

Written Opinion for PCT/US02/31128; Sep. 2002; Applicant: Vertis Neuroscience, Inc. (6 pgs).

Written Opinion for PCT/US03/03678; Dec. 2003; Applicant: Northstar Neuroscience, Inc. (4 pgs.).

Written Opinion for PCT/US02/32695; Jun. 2003; Applicant: Vertis Neuroscience, Inc. (2 pgs).

Written Opinion for PCT/US02/31127; May 2003; Applicant: Vertis Neuroscience, Inc. (2 pgs).

Written Opinion for PCT/US02/31112; Aug. 2003; Applicant: Vertis Neuroscience, Inc. (5 pgs).

Written Opinion for PCT/US02/07077; Jul. 2003; Applicant: Vertis Neuroscience, Inc. (4 pgs).

Deuschl, Gunther, "Essential Tremor," orphanet, Dec. 2003, 4 pgs; http://www.orpha.net/data/patho/GB/uk–essential-tremor.pdf.

Hummel, Friedhelm et al., "Effects of non–invasive cortical stimulation on skilled motor function in chronic stroke," Brain Advance Access, Jan. 5, 2005, pp. 1–10, Brain.

Lang, Nicolas et al., "Preconditioning with Transcranial Direct Current Stimulation Sensitizes the Motor Cortex to Rapid–Rate Transcranial Magnetic Stimulation and Controls the Direction of After–Effects, " Biol Psychiatry 2004:56:634–639, 2004 Society of Biological Psychiatry.

Nitsche, Michael A. et al., "Level of action of cathodal DC polarisation induced inhibition of the human motor cortex," Dec. 2, 2002, Clinical Neurophysiology 114 (2003) 600–604.

Nitsche, Michael A., et al., "Facilitation of implicit Motor Learning by Weak Transcranial Direct Current Stimulation of the Primary Motor Cortex in the Human," Journal of Cognitive Neuroscience 15:4, pp. 619–626, 2003 Massachusetts Institute of Technology.

Paulus, W, "Transcranial direct current stimulation (tDCS)", Transcranial Magnetic Stimulation and Transcranial Direct Current Stimulation (Supplements to Clinical Neurophysiology; vol. 56), pp. 249–254, 2003 Elsevier Science, B.V.

* cited by examiner

METHODS FOR TREATING ESSENTIAL TREMOR

CROSS-REFERENCE TO RELATED APPLICATIONS

The present application claims priority to pending U.S. Provisional Application 60/432,073, entitled "System and Method for Treating Parkinson's Disease and other Movement Disorders," filed Dec. 9, 2002.

TECHNICAL FIELD

The present invention is directed toward systems and methods for treating essential tremor, associated with abnormal neural activity in the brain.

BACKGROUND

A wide variety of mental and physical processes are controlled or influenced by neural activity in particular regions of the brain. For example, various physical or cognitive functions are directed or affected by neural activity within the sensory or motor cortices. Across most individuals, particular areas of the brain appear to have distinct functions. In the majority of people, for example, the areas of the occipital lobes relate to vision; the regions of the left interior frontal lobes relate to language; portions of the cerebral cortex appear to be consistently involved with conscious awareness, memory, and intellect; and particular regions of the cerebral cortex as well as the basal ganglia, the thalamus, and the motor cortex cooperatively interact to facilitate motor function control.

Essential tremor is a frequently occurring, complex neurologic movement disorder. At this time, the causes of essential tremor are not well understood.

Essential tremor (or ET) typically affects the hands, but it can also affect the head and neck (causing shaking), the face, jaw, tongue, voice, trunk, and, on occasion, the legs and feet. The tremor can take the form of a rhythmic lateral motion or forward and aft motion produced by involuntary muscle contractions. The duration and intensity of the tremors can vary substantially from one day to the next and during the course of a given day. ET typically has two forms: postural tremor, which occurs when the patient holds the affected muscle in a particular position, and kinetic tremor, which occurs when the patient moves the affected muscle in a particular way. Most patients affected by ET have both postural and kinetic tremor symptoms.

Effectively treating ET can be very difficult. Current treatments for ET symptoms include drugs, surgical intervention, and/or neural stimulation. Drug treatments or therapies may involve the administration of a beta-adrenergic blocker or anticonvulsant medication to the patient. Drug therapies may involve propanolol, mysoline, primidone, benzodiazepine, or a weak solution of botulinum toxin A. Unfortunately, many patients cannot tolerate or fail to adequately respond to drug therapies.

Surgical intervention for ET typically includes a thalamotomy, a procedure that involves ablating or destroying a selected portion of the thalamus. Unfortunately, surgical intervention is a very time consuming and highly invasive procedure. Potential complications associated with the procedure include risk of hemorrhage, stroke, and/or paralysis. Furthermore, because the procedures permanently destroy neural tissue, the effects of such intervention cannot be readily adjusted or "fine tuned" over time.

Neural stimulation treatments have shown promising results for reducing some of the symptoms associated with ET. Neural activity is governed by electrical impulses or "action potentials" generated in and propagated by neurons. While in a quiescent state, a neuron is negatively polarized and exhibits a resting membrane potential that is typically between −70 and −60 mV. Through chemical connections known as synapses, any given neuron receives excitatory and inhibitory input signals or stimuli from other neurons. A neuron integrates the excitatory and inhibitory input signals it receives, and generates or fires a series of action potentials in the event that the integration exceeds a threshold potential. A neural firing threshold, for example, may be approximately −55 mV. Action potentials propagate to the neuron's synapses and are then conveyed to other synaptically connected neurons.

Neural activity in the brain can be influenced by neural stimulation, which involves the application of electrical and/or magnetic stimuli to one or more target neural populations within a patient using a waveform generator or other type of device. Various neural functions can thus be promoted or disrupted by applying an electrical current to one or more regions of the brain. As a result, researchers have attempted to treat certain neurological conditions, including ET, using electrical or magnetic stimulation signals to control or affect brain functions.

Deep Brain Stimulation (DBS) is a neural stimulation therapy that has been used as an alternative to drug treatments and ablative surgical therapies. In DBS, one or more electrodes are surgically implanted into the brain proximate to deep brain or subcortical neural structures. For treating ET, an electrode is typically positioned in or proximate to the ventrointermediate nucleus (VIM) of the thalamus. In a typical DBS system, a pulse generator delivers a continuous or essentially continuous electrical stimulation signal having a pulse repetition frequency of approximately 150 Hz to each of two deep brain electrodes. U.S. Pat. No. 5,883,709 discloses one conventional DBS system for treating movement disorders.

Although DBS therapies may significantly reduce ET symptoms, particularly when combined with drug treatments, they are highly invasive procedures. In general, configuring a DBS system to properly function within a patient requires a time consuming, highly invasive surgical procedure for implanting at least one, and possibly two, DBS electrodes. DBS surgical procedures have essentially the same risks as those described above for ablative surgical intervention.

Motor Cortex Stimulation (MCS) is another type of brain stimulation treatment that has been proposed for treating movement disorders, such as ET and Parkinson's disease. MCS involves the application of stimulation signals to the motor cortex of a patient. One MCS system includes a pulse generator connected to a strip electrode that is surgically implanted over a portion of only the motor cortex (precentral gyrus). The use of MCS to treat symptoms associated with Parkinson's Disease is described in Canavero, Sergio, "*Extradural Motor Cortex Stimulation for Advanced Parkinson's Disease: Case Report*," Movement Disorders (Vol. 15, No. 1, 2000).

Because MCS involves the application of stimulation signals to surface regions of the brain rather than deep neural structures, electrode implantation procedures for MCS are significantly less invasive and time consuming than those for DBS. As a result, MCS may be a safer and simpler alternative to DBS for treating ET symptoms. Present MCS techniques, however, fail to address or adequately consider a variety of factors that may enhance or optimize the extent to which a patient experiences short term and/or long term relief from ET symptoms.

DETAILED DESCRIPTION

The following disclosure describes several embodiments and systems for treating essential tremor and other movement disorders using cortical stimulation. Several features of methods and systems in accordance with embodiments of the invention are set forth and described in FIGS. 1A–7B. It will be appreciated that methods and systems in accordance with other embodiments of the invention can include additional procedures or features different than those shown in FIGS. 1A–7B. Additionally, methods and systems in accordance with several embodiments of the invention may not include all of the features shown in these Figures. Throughout the Figures, like reference numbers refer to similar or identical components or procedures.

Figure 1A:
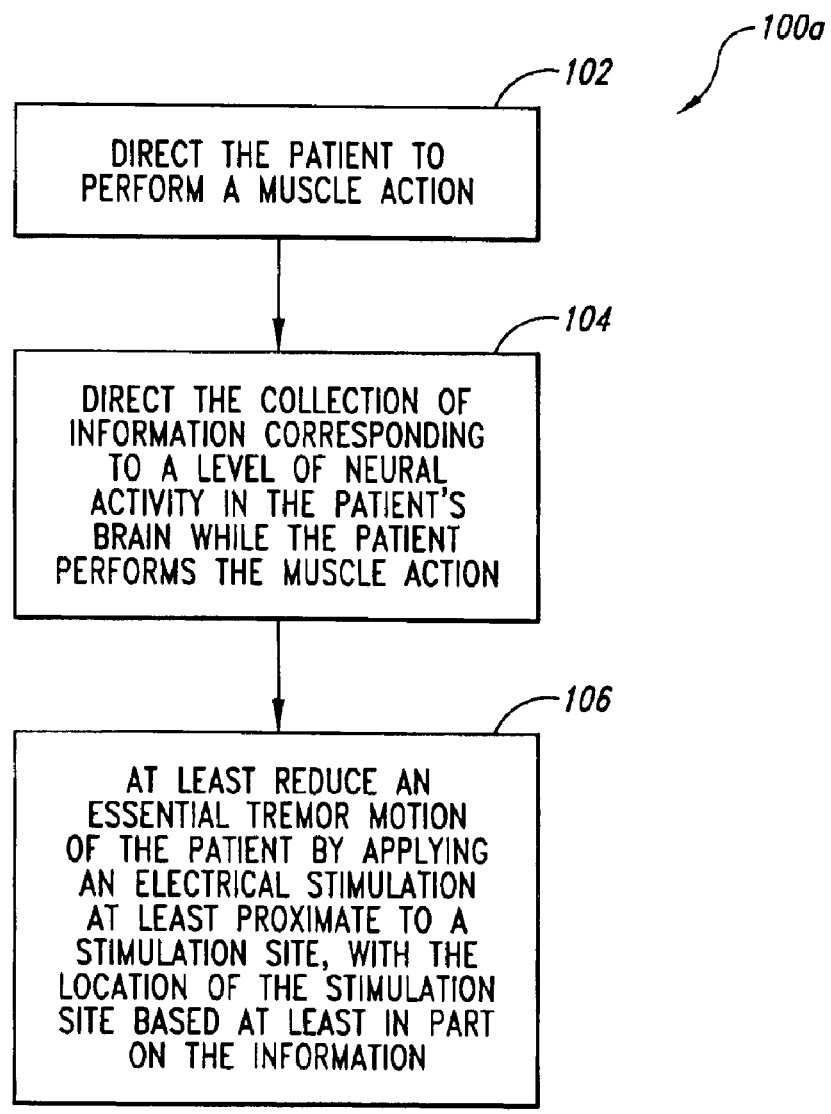
FIGS. 1A–1B are flow charts illustrating methods for treating essential tremor in accordance with several embodiments of the invention.

FIG. 1A is a flow chart illustrating a method for treating essential tremor in accordance with an embodiment of the invention. In one embodiment, a method 100a for treating essential tremor includes directing a patient to perform a muscle action (method portion 102). The muscle action can include maintaining the muscle in a certain position, and/or moving the muscle in a certain manner. The method 100a can further include directing the collection of information corresponding to a level of neural activity in the patient's brain while the patient performs the muscle action (method portion 104). In one aspect of this embodiment, method portion 104 can be performed at least in part by a human operator, for example, a technician or doctor who operates an imaging system. In another aspect of this embodiment, the process of directing the collection of information can be performed partially or entirely by a computer, for example, by a hardware and/or software based routine that collects the information corresponding to the level of neural activity. In either embodiment, the information can take several forms, and/or can correspond to the level of neural activity in the patient's brain by way of several techniques, as described in greater detail below with reference to FIG. 1B.

In process portion 106, the method 100a includes at least reducing an essential tremor motion of the patient by applying an electrical stimulation at least proximate to a stimulation site, with the location of the stimulation site based at least in part on the information collected in method portion 104. For example, an operator and/or a computer-based set of instructions can apply an electrical stimulation to one or more electrodes or electrical contacts placed within the patient's brain. Further aspects of this and other embodiments of process portion 106 are also described in greater detail below with reference to FIG. 1B.

Figure 1B:
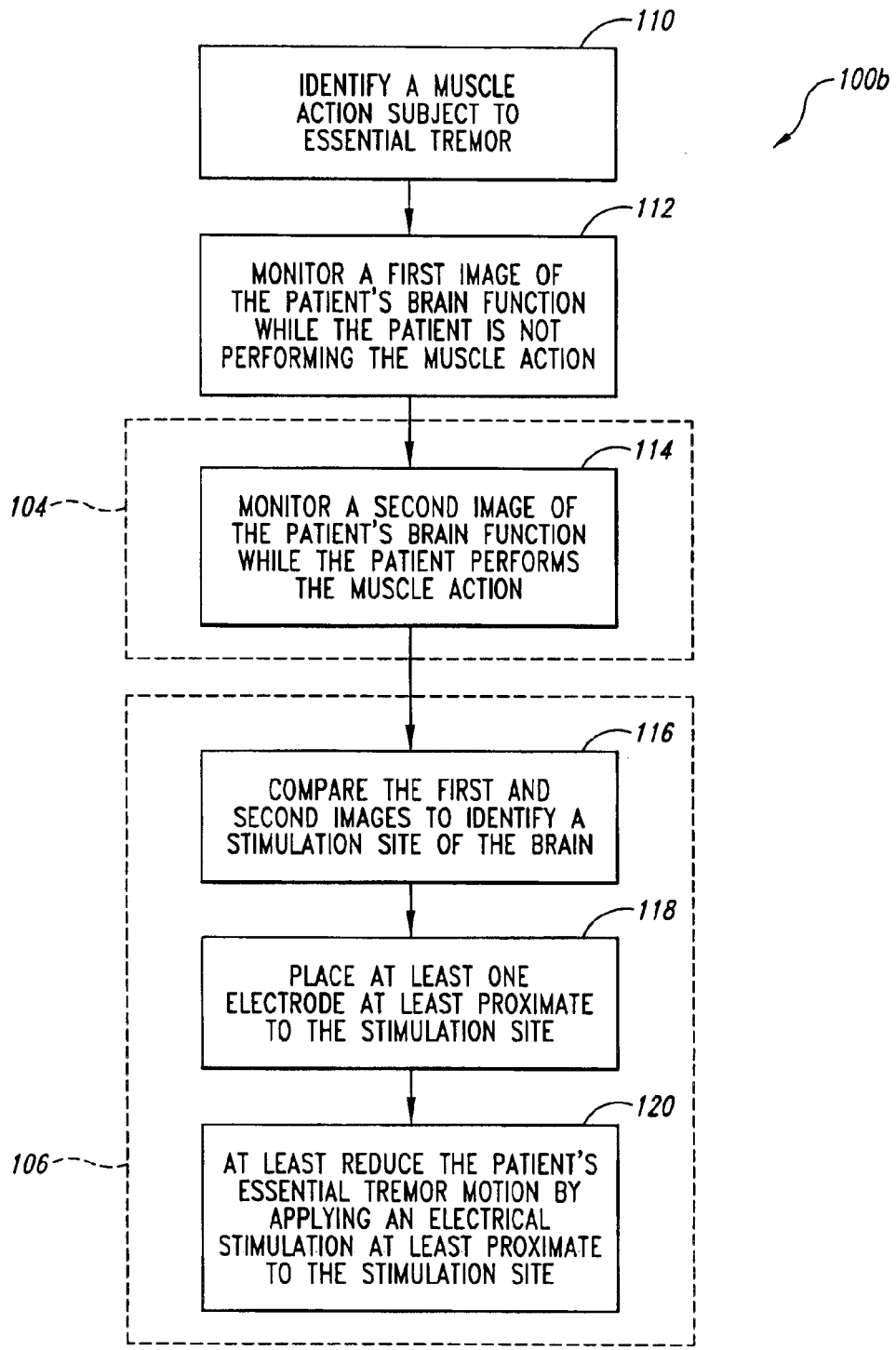

FIG. 1B is a flow chart illustrating a method 100b for treating essential tremor in accordance with another embodiment of the invention. The method 100b includes further details of collecting information (method portion 104, FIG. 1A) and reducing essential tremor motion (method portion 106, FIG. 1A) associated with this embodiment. In one aspect of this embodiment, the method 100b can include identifying a muscle action subject to essential tremor (method portion 110). For example, a practitioner can direct the patient to perform a variety of movements, (e.g., for kinetic tremor) and/or assume a variety of positions (e.g., for postural tremor) while the practitioner observes the patient for an indication of essential tremor motion. Based on the results of this activity, the practitioner can single out one or more muscle actions that manifest essential tremor behavior or motion.

In method portion 112, the practitioner can monitor a first or baseline image of the patient's brain function while the patient is not performing the muscle action identified in method portion 110 (e.g., while the patient or relevant patient muscles are generally at rest, or the patient avoids performing the muscle action). In one embodiment, the first image can be generated using functional magnetic resonance imaging (fMRI) techniques, magnetic resonance imaging (MRI) techniques, or computed tomography (CT) techniques. In a particular aspect of this embodiment, the first image can be generated by fMRI techniques that determine the level of the patient's brain function based on a measurement of blood oxygen levels in the patient's brain. In other embodiments, the level of the patient's brain function is ascertained by other techniques. In any of these embodiments, the first image can include an image of a portion of the patient's brain upon which is superimposed some indication of the brain activity level. For example, the image can be color-coded to distinguish parts of the brain having a high level of activity (e.g., presented in one color) from portions of the brain having a relatively low level of activity (e.g., presented in another color). The image can include an image of the relative position between external markers and at least one of the central sulcus, precentral gyrus, and/or the postcentral gyrus of a patient. The external markers can be anatomical features of the patient (e.g., the patient's nose bridge or ear canal) or fiducials that are attached to the patient. For example, the external markers can be fiducials that are attached to the skull of the patient.

In method portion 114, the practitioner can monitor a second image of the patient's brain function while the patient performs the muscle action identified in method portion 110. In a particular aspect of this embodiment, the technique used to generate the second image is at least approximately identical to the technique used to produce the first image. Accordingly, the two images can be easily compared.

In method portion 116, the first and second images are compared to identify a stimulation site of the brain. For example, if a particular portion of the brain shows activity when the patient executes an essential tremor motion or assumes an essential tremor posture, this region can be identified by comparing the first image with the second image. In some cases, a portion of the brain responsible for coordinating the muscle movement required to execute the motion or assume the posture may also be a portion of the brain responsible for generating the tremor motion itself. In other embodiments, the correlation between the portions of the brain responsible for these two functions may be less clear. In these situations, the practitioner may use additional techniques (described in greater detail below with reference to FIGS. 7A–7B) to isolate the site responsible for tremor motion. In any of these embodiments, the stimulation site can be generally proximate to the dura of the patient and can be positioned over at least the precentral gyrus of the cortex. In particular embodiments, the stimulation site can also be located over the central sulcus and/or the postcentral gyrus of the patient. In any of these embodiments, the methods 100a and 100b result in an accurate determination of the location of the underlying cortical features relative to external landmarks on the patient. As explained in more detail below, this is expected to significantly improve the efficacy of stimulation therapies for treating ET.

In method portion 118, the practitioner can place at least one electrode at least proximate to the stimulation site determined in method portion 116. In method portion 120, the patient's essential tremor motion is reduced or eliminated by applying an electrical stimulation at least proximate to the stimulation site. The neural stimulation can be an electrical current applied epidurally or subdurally to the stimulation site. When the neural stimulation is an electrical current applied directly to the cerebral cortex proximate to the dura, the method 100b can include implanting an electrode at least proximate to the dura at the stimulation site. In other embodiments, the neural stimulation can be transcutaneous magnetic stimulation. Several aspects of electrodes, placement techniques, and stimulation techniques in accordance with particular embodiments of the invention are described in more detail below with respect to FIGS. 2A–7B.

Figure 2A:
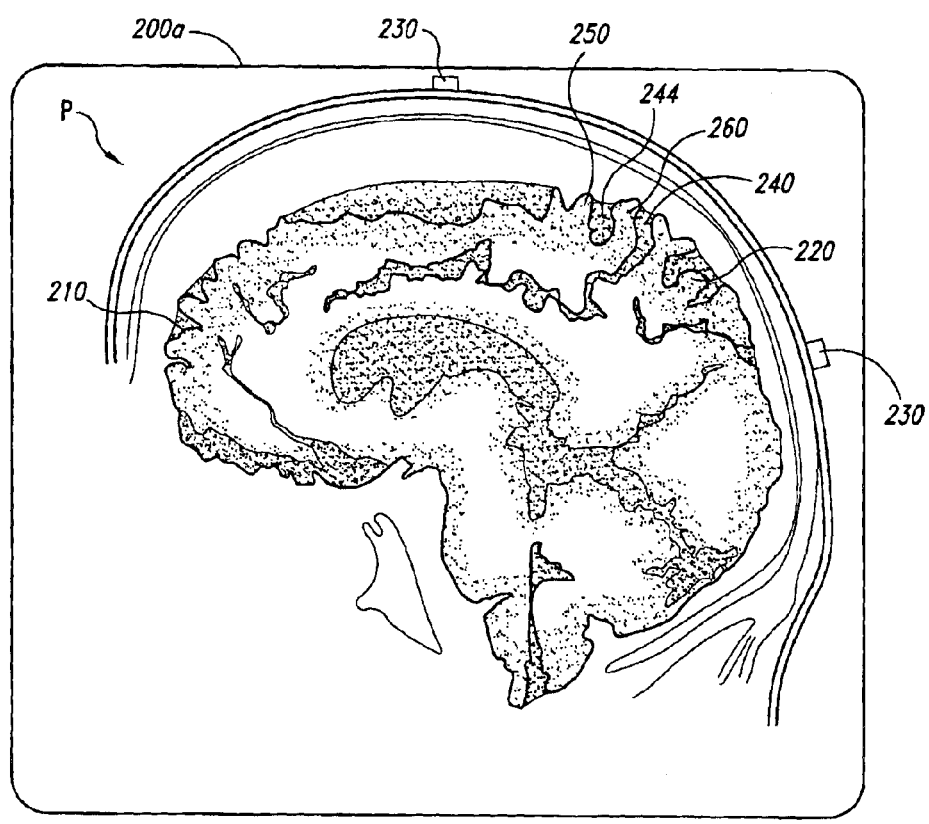
FIG. 2A is an image showing a mid saggital section of a brain of a patient.
Figure 2B:
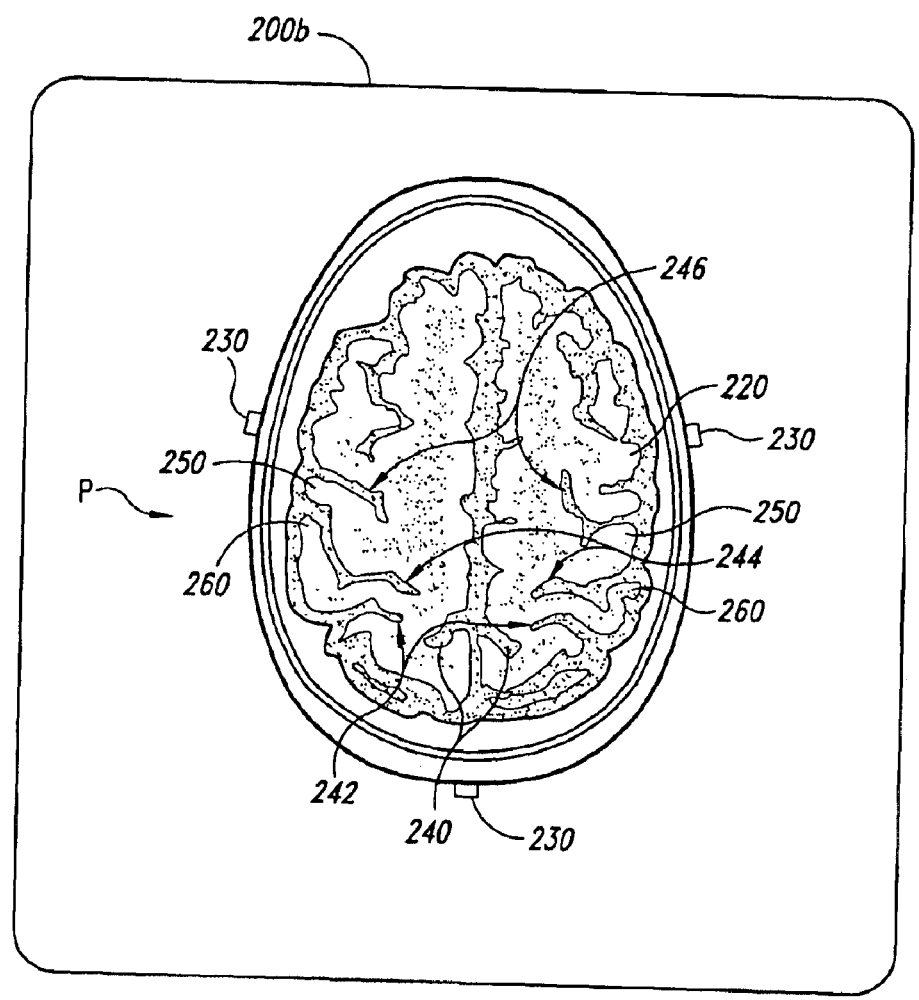
FIG. 2B is an image showing an axial view of a portion of the cerebral cortex of the brain of the patient.

FIGS. 2A and 2B are examples of images corresponding to method portions 104, 112 and 114 (FIG. 1B). FIG. 2A is a magnetic resonance image 200a showing a view of the brain 210 of a patient P taken along a mid saggital section. The image 200a shows the location of various features of the cerebral cortex 220 relative to fiducial markers 230 attached to the skull of the patient P. In one embodiment, the pars marginalis sulcus 240 of the cortex 220 is located using the image 200a of the mid saggital section. This particular image is useful because the pars marginalis sulcus is the only sulcus that can be followed into the interhemispheric fissure in this view. Based on the location of the pars marginalis sulcus shown in image 200a, this position can be extrapolated to an axial image to determine the location of the central sulcus, the postcentral gyrus, and the precentral gyrus on the cortex 220 relative to the external markers.

In a further aspect of an embodiment of the methods 100a, 100b described above, an axial image of the cortex 220 is generated. FIG. 2B is a magnetic resonance image 200b of a brain of a patient taken along an axial section. Referring to FIG. 2B, the pars marginalis sulcus 240 appears as a small, symmetrical sulcus extending bilaterally out from the interhemispheric fissure. Based upon the position of the pars marginalis sulcus 240, the position of the postcentral sulcus 242 can be determined by moving laterally (i.e., outward) from the pars marginalis sulcus 240. The postcentral sulcus 242 forms the posterior boundary of the postcentral gyrus 260, and thus the central sulcus 244 can be identified as the anterior boundary of the postcentral gyrus 260. Similarly, the central sulcus 244 forms the posterior boundary of the precentral gyrus 250 and the precentral sulcus 246 forms the anterior boundary of the precentral gyrus 250.

Identifying a stimulation site of the brain (method portion 116, FIG. 1B) can also include identifying an external region on the patient relative to the location of the central sulcus 244. After identifying the location of the central sulcus 244 on the image 200b, the location of the central sulcus 244 is noted relative to the external markers 230. Using standard neuronavigational MRI techniques, the data from the images can be transferred into an intraoperative navigational station that locates the external position on the scalp of the patient overlying the central sulcus 244 relative to the position of the fiducial markers 230. The external position accordingly defines the general area where stimulation will be applied. The actual stimulation site is generally under the scalp at an area that is proximate to the dura of the patient and aligned with the external position identified on the patient.

FIGS. 2A–2B refer to specific process portions (e.g., process portion 112 and 114) described above with reference to FIG. 1B that include monitoring images of the patient's brain. In other embodiments, the method portion of directing the collection of information corresponding to a level of neural activity in the patient's brain while the patient performs a muscle action (e.g., method portion 104, FIG. 1A) can be completed without generating an image. For example, fMRI, MRI, or CT techniques can be used to generate a digital representation of brain activity without necessarily generating a visible image. In a particular aspect of this embodiment, an algorithm or other computer-based method can be used to determine the stimulation site, based upon the digital representation described above. In either of these embodiments, the patient can receive electrical stimulation at the stimulation site via implanted electrodes. Techniques for placing the electrodes at the stimulation site are described in greater detail below with reference to FIGS. 3A–3C.

Figure 3A:
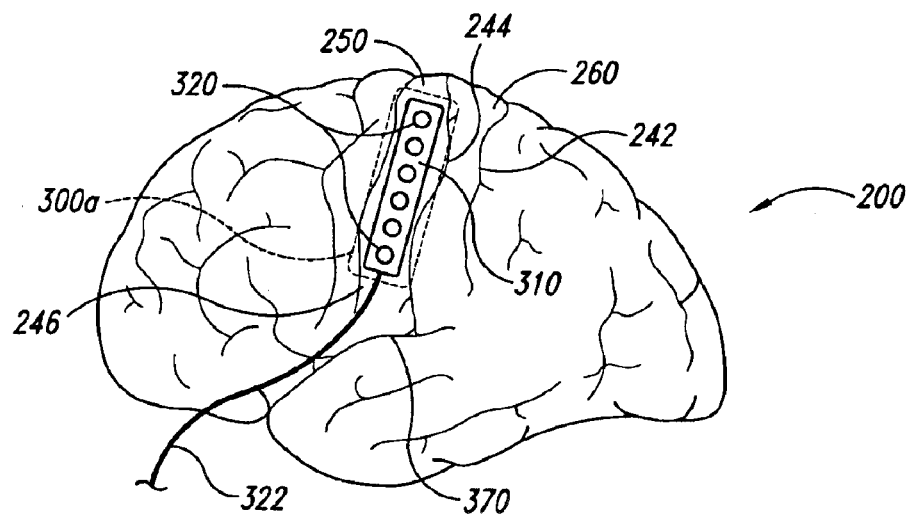
FIG. 3A is a side view of a brain of a patient with an electrode array implanted in accordance with one embodiment of the invention.
Figure 3B:
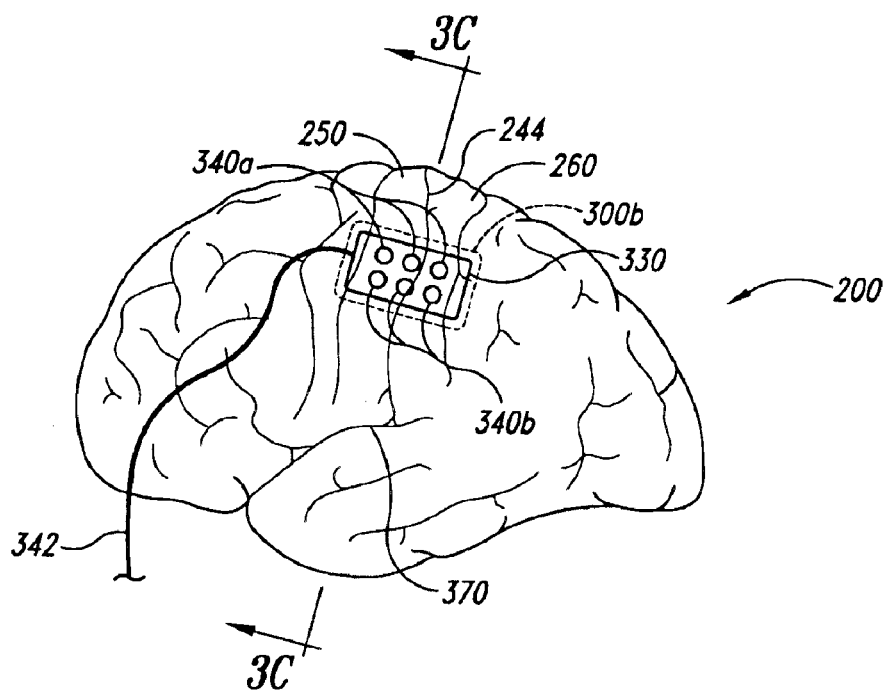
FIG. 3B is a side view of a brain of a patient with an electrode array implanted in accordance with another embodiment of the invention.

FIGS. 3A–3B illustrate several embodiments of the process portion 118 (FIG. 1B) which includes placing at least one electrode at least proximate to a stimulation site. FIG. 3A, more specifically, is a schematic side view of the brain 200 illustrating a technique for implanting a linear electrode array 310 at a stimulation site 300a proximate to the dura and over the precentral gyrus 250, in accordance with an embodiment of the invention. In one aspect of this embodiment, the linear electrode array 310 has a plurality of electrodes 320 arranged along a single row. In other embodiments the linear electrode array 310 may have only one electrode 320. The electrodes 320 can be circular contacts each having a surface area of approximately 5 mm$^2$ and being spaced apart by about 7.5 mm. In other embodiments, the electrodes can be other shapes and have other configurations, for example, those disclosed in pending U.S. application Ser. No. 10/742,579, entitled "Apparatuses and Systems for Applying Electrical Stimulation to a Patient," filed Dec. 18, 2003 and incorporated herein by reference. In one aspect of an embodiment shown in FIG. 3A, the linear electrode array 310 has a lead 322 coupled to the electrodes 320 and an implanted pulse generator implanted above the neck or at a subclavicular location. The lead 322 is tunneled through the patient using standard techniques.

The linear electrode array 310 can be positioned so that the row of electrodes 320 extends in a medial to lateral direction generally parallel with the central sulcus 244. The electrodes 320 are also superimposed over the precentral gyrus 250. The linear electrode array 310 generally has a plurality of electrodes 320 to provide extensive coverage over the precentral gyrus 250 and thus activate a large number of neurons in the motor cortex (e.g., use all of the electrodes) or only discrete populations of neurons in the motor cortex with only a single implantation of an electrode array (e.g., activate only selected electrodes). The electrode array 310 can be implanted so that the electrodes are proximate to the dura such as at an epidural or subdural location.

FIG. 3B is a side-view of the brain 200 illustrating another embodiment for implanting an electrode array proximate to the dura at the stimulation site. In this embodiment, the stimulation site 300b is located over the precentral gyrus 250 and the postcentral gyrus 260. A grid electrode array 330 is implanted at the stimulation site 300b proximate to the dura. The grid electrode array 330 can include a plurality of first electrodes 340a arranged along a first row and a plurality of second electrodes 340b arranged along a second row. The first and second rows of electrodes 340a–b can extend generally at an oblique angle relative to the central sulcus 244. The grid electrode array 330 also has a lead 342 coupled to the electrodes 340a–b and an implanted pulse generator. As with the linear electrode array 310, the grid electrode array 330 can be implanted so that the electrodes are proximate to the dura.

One aspect of several embodiments of the invention is that the stimulation sites 300a and 300b shown on FIGS. 3A and 3B may be located relative to the precentral gyrus 250, the central sulcus 244, and/or the postcentral gyrus 260 using the information collection and site selection procedures described above with reference to FIGS. 1A–2B. This enables the stimulation to be applied to desired locations on the cortex with much greater accuracy than previous methods that rely solely on the external anatomical features of the patient. The greater precision of locating the stimulation sites 300a–b for implanting the electrode arrays is expected to enhance the efficacy of stimulation treatments for treating essential tremor.

Figure 4:
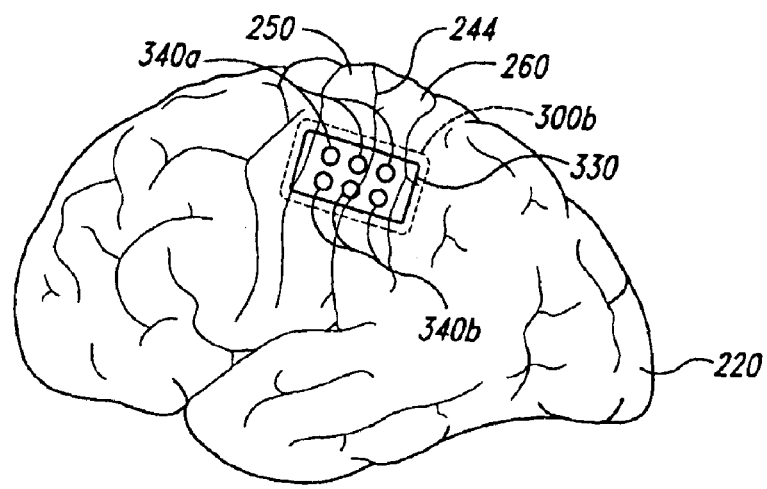
FIG. 4 is a side view of a brain of a patient showing one arrangement for applying neural stimulation to treat essential tremor.

FIG. 4 is a side view illustrating several embodiments of applying neural stimulation directly to the stimulation site. More specifically, FIG. 4 illustrates the grid electrode array 330 positioned at the stimulation site 300b over the precentral gyrus 250, the central sulcus 244, and the postcentral gyrus 260. The neural stimulation can include passing an electrical current through the electrodes 340a–b to the stimulation site 300b. In one embodiment, the electrical current can be applied to a single one of the electrodes 340a or 340b to provide a monopolar pulse of current to a small area of the cortex 220. A return electrode can be positioned elsewhere in the patient, such as on the other side of the patient's brain or at a subclavicular location. The return electrode can be a portion of a pulse generator or another electrode implanted elsewhere in the patient. In other embodiments, electrical current can be passed through all of the electrodes 340a–b or only a subset of these electrodes to activate larger or different populations of neurons. In these embodiments, the potential applied to the electrodes 340a–b can be the same across all of the activated electrodes to provide monopolar stimulation at the stimulation site. This embodiment also typically has a return electrode implanted elsewhere in the patient as explained above. In other embodiments, some of the electrodes can be biased with a positive polarity and other electrodes can be biased with a negative polarity. For example, the first electrodes 340a can be biased with one polarity and the second electrodes 340b can be biased with an opposite polarity. This embodiment provides a bipolar stimulation to the cortex 220. The particular configuration of the electrodes can be optimized after implantation to provide the most efficacious therapy for the patient.

The particular waveform of the stimuli depends upon the symptoms of the particular patients. In one embodiment, the stimulus can have a waveform with a voltage of approximately 0.25 V–5.0 V, a pulse duration of approximately 20 microseconds–500 milliseconds, and a frequency of approximately 10 Hz–200 Hz. In other embodiments, the electrical stimulus can have a voltage of 0.5 V–3.5 V, a pulse duration of 100 microseconds–200 microseconds, and a frequency of approximately 20 Hz–50 Hz. In still other embodiments, the voltage of the waveform can be approximately 2.0–3.5 V, and more particularly approximately around 3 V. Additionally, the pulse duration can be in the range of 90–180 microseconds. The stimulus can be applied for a period of 0.5 hour–4.0 hours, and in many applications the therapy is applied for a period of approximately 0.5 hour–1.5 hours. In other embodiments, the stimulation can be applied continuously, or only during waking periods but not sleeping periods. Examples of specific stimulation protocols for use with an electrode array at an epidural stimulation site over the precentral gyrus are as follows:

Example 1

An electrical stimulus having a voltage of approximately 2.1 V, an impedance of 600 to 1000 Ohms, a pulse duration of 160 microseconds, and a frequency of approximately 130 Hz. The therapy is not applied continuously, but rather during 30–60 minute intervals.

Example 2

The stimulus has a voltage amplitude of approximately 3 V–3.5 V, a pulse duration of approximately 150–180 microseconds, and a frequency of approximately 25 Hz–31 Hz. The stimulus is applied continuously during waking periods, but it is discontinued during sleeping periods to conserve battery life of the implanted pulse generator.

Example 3

The stimulus has a voltage of approximately 3.0 V, a pulse duration of approximately 90 microseconds, and a frequency of approximately 30 Hz. This stimulus is applied continuously during waking and sleeping periods, but it can be discontinued during sleeping periods.

Figure 5:
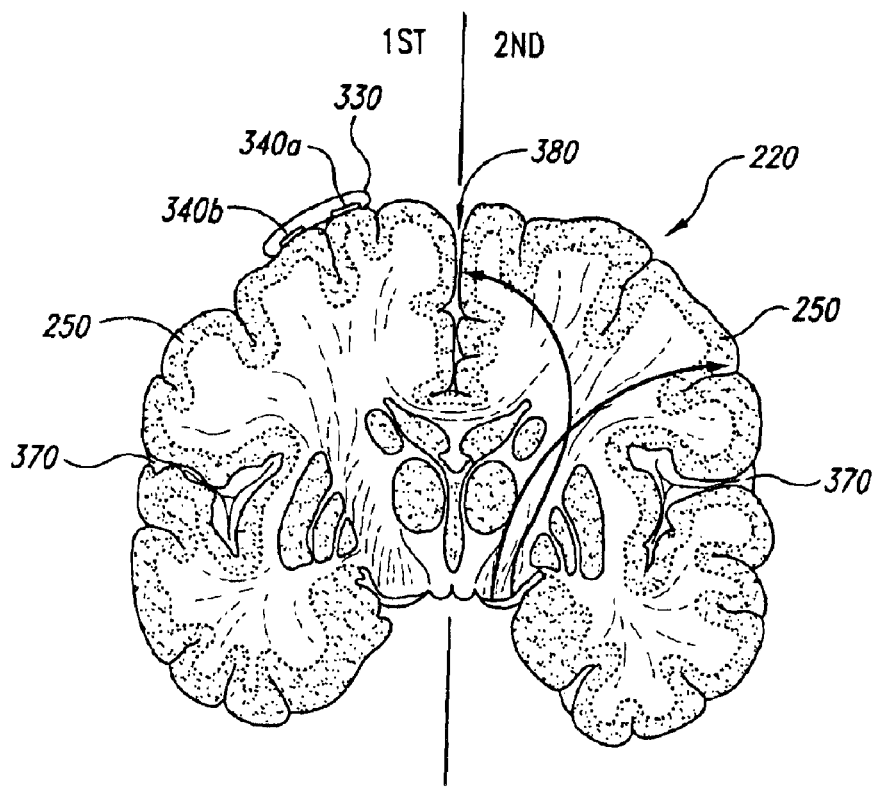
FIG. 5 is a cross-sectional view of the cerebral cortex of a patient illustrating an arrangement for treating essential tremor in accordance with another embodiment of the invention.

FIG. 5 illustrates another aspect of an embodiment of the invention. In many cases of essential tremor, the symptoms are manifested to a greater extent on one side of the body than the other. For example, a patient may have a tremor in both hands, but usually one hand will have a tremor worse than the other hand. In this embodiment, the patient's body is divided into a first side and a second side opposite the first side relative to a medial axis (e.g., right side-left side), and only one side of the cortex is stimulated to treat the disorder on both sides of the body. This embodiment can be carried out by implanting the electrode array 330 (or 310) at a stimulation site on only the first side of the patient when the disorder of a motor function is greater on the second side of the patient. The single electrode array can provide a bilateral affect that not only treats the disorder associated with the second side of the patient, but also treats the disorder associated with the first side of the patient. For example, if the patient experiences a bilateral tremor that is worse on the right side compared to the left side, then an electrode array can be implanted proximate to the dura over only the left hemisphere of the cortex 220. The bilateral effect of the single-side stimulation may be enhanced using unipolar, monopolar, or isopolar stimulation techniques in which one or more nonfloating electrodes 320 are biased at an identical polarity. The bilateral effect may be caused by activation of commissural neurons (large pyramidal cells) in the deep portion of layer III of the motor cortex. Subsequent to activation, these neurons can depolarize complimentary cell groups in the contralateral hemisphere via the corpus callosum. By accurately locating the electrodes over the precentral gyrus using the information collection and site selection procedures described above, the electrode may maximally affect the contralateral lower extremity musculature and also the ipsilateral muscle groups. It is expected that the placement should be sufficiently remote from the interhemispheric fissure to avoid venous damage or occlusion. As a result, the single-side stimulation site may be particularly advantageous in certain situations because it requires only a single electrode array to be planted relative to a single hemisphere of the cortex 220 of the patient. This reduces the invasiveness and the risk associated with surgery.

Figure 6:
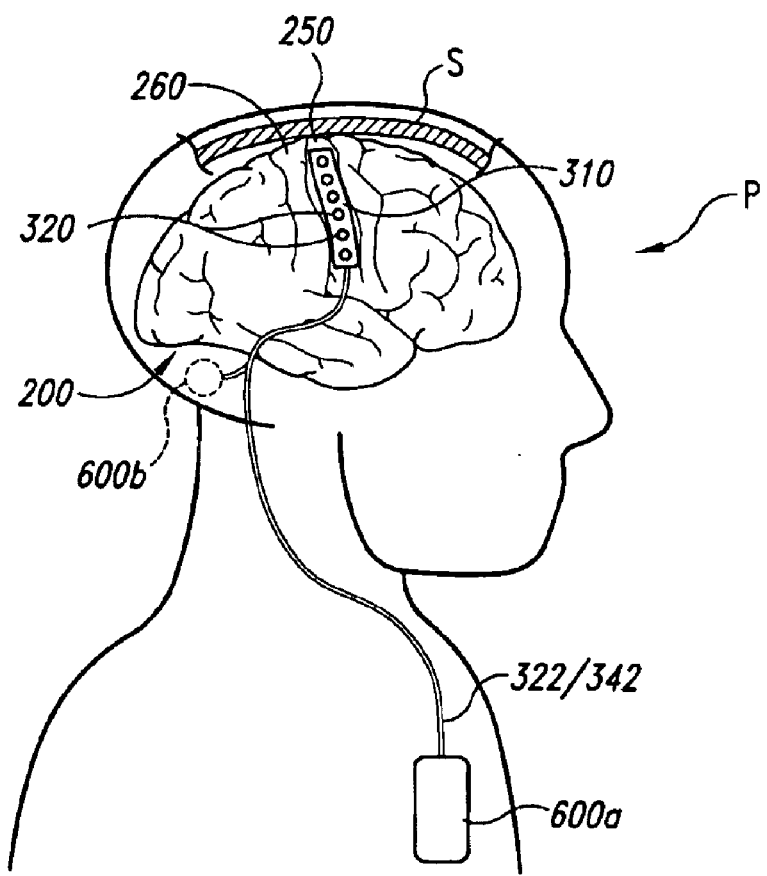
FIG. 6 is a schematic view illustrating a system for treating essential tremor in accordance with still another embodiment of the invention.

FIG. 6 is a schematic view illustrating a system for treating essential tremor in accordance with an embodiment of the invention. The system can include the linear electrode array 310 coupled to an implanted pulse generator 600a implanted at a subclavicular location in the patient P. The grid electrode array 330 can be substituted for the linear electrode array 310. In either of these embodiments, a lead 322/342 is tunneled between the implanted pulse generator 600a and the electrode array. In another embodiment, the system has an implanted above-neck pulse generator 600b that is smaller and configured to be implanted at a location above the neck of the patient P. The above-neck implanted pulse generator 600b can be planted posteriorly of the ear of the patient P. In each of these embodiments, the electrode arrays 310 or 330 (not shown in FIG. 6) are implanted underneath the skull S of the patient P at an epidural or subdural stimulation site as set forth above.

Figure 7A:
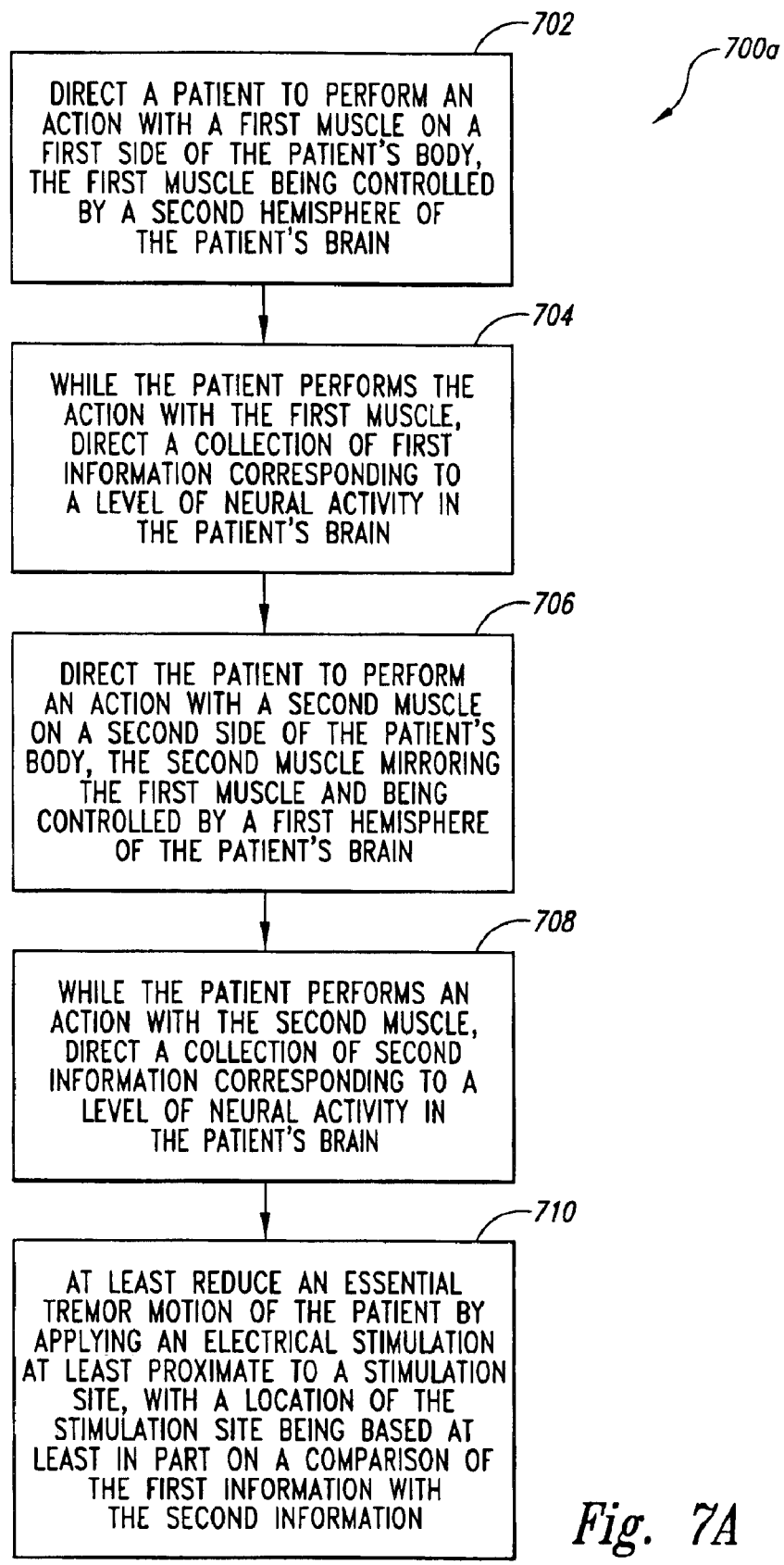
FIGS. 7A–7B are flow charts illustrating methods for treating essential tremor in accordance with yet further embodiments of the invention.
Figure 7B:
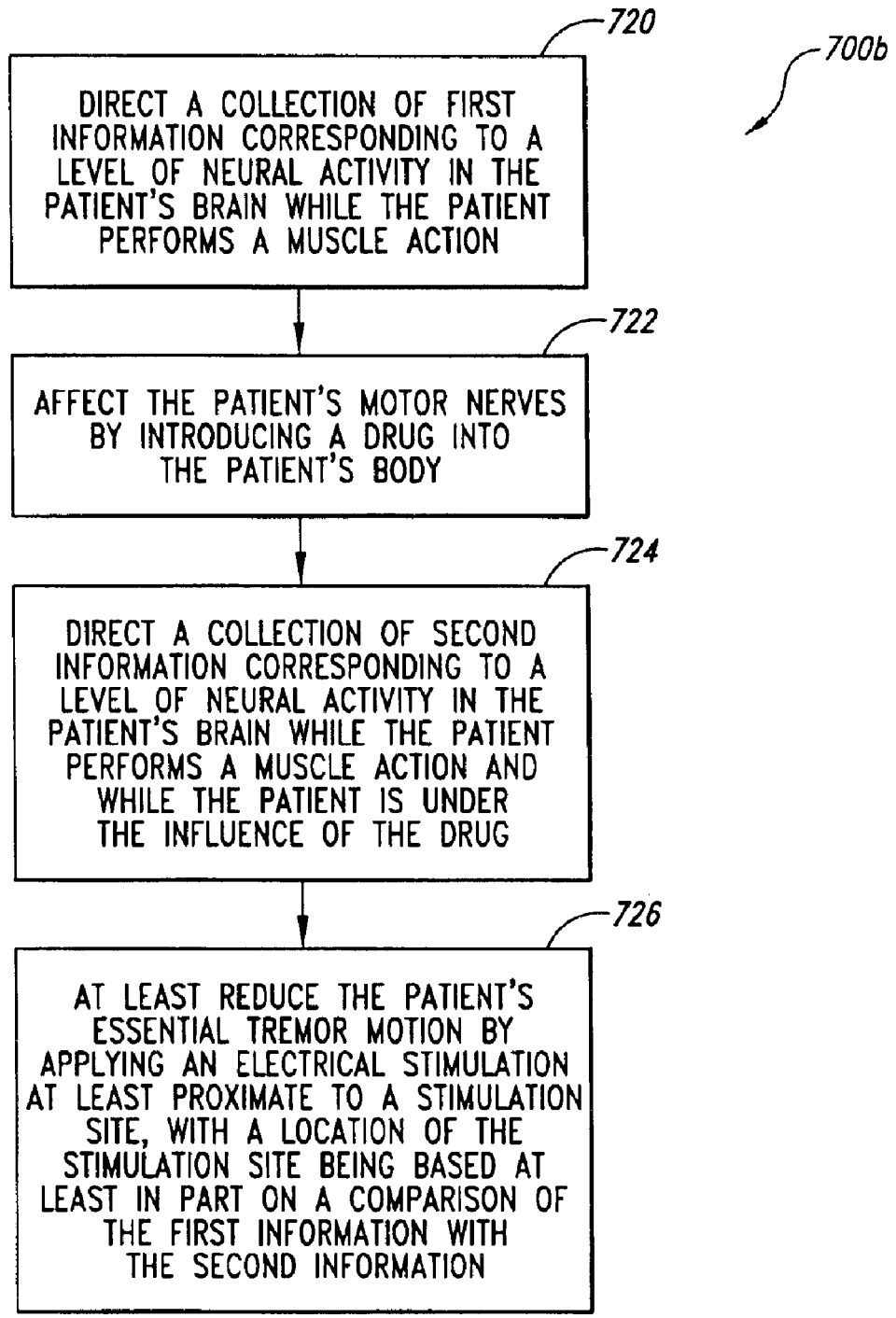

FIGS. 7A–7B illustrate methods for treating essential tremor in accordance with further embodiments of the invention. Beginning with FIG. 7A, a method 700a includes directing a patient to perform an action with a first muscle on a first side of the patient's body, with the first muscle being controlled by a second hemisphere of the patient's brain (method portion 702). The action can include holding the muscle at a particular position or moving the muscle in a particular manner. The method further includes (while the patient performs the action with the first muscle) directing the collection of first information corresponding to a level of neural activity in the patient's brain (method portion 704). The patient is then directed to perform an action with a second muscle on a second side of the patient's body, the second muscle mirroring the first muscle and being controlled by the first hemisphere of the patient's brain (method portion 706). While the patient performs an action with the second muscle, the method 700a can include directing the collection of second information corresponding to a level of neural activity in the patient's brain (method portion 708). In method portion 710, an essential tremor motion of the patient is reduced or eliminated by applying an electrical stimulation at least proximate to a stimulation site. The stimulation site is located based at least in part on a comparison of the first information with the second information.

In a particular aspect of an embodiment of the method 700a described above, a practitioner can make use of the frequent tendency of the patient to manifest essential tremor symptoms on one side of the body more than on the other. For example, if the patient has more essential tremor motion associated with movement of the left hand than with the right hand, the practitioner can ask the patient to move the left hand and then view an image of the right side of the patient's brain while the patient undergoes the directed movement. The practitioner can then direct the patient to move the right hand while viewing an image of the left hemisphere of the patient's brain. By comparing the two images, the practitioner can attribute common aspects of the active areas of the images to brain activity associated with non-essential tremor movement, and differences between active areas of the images with motion related to essential tremor. For example, in a particular embodiment, the common aspects of the images can include common areas or volumes indicated to have heightened neural activity. In other embodiments, the common aspects can include areas or volumes that have the same level of heightened neural activity. In either embodiment, the practitioner can compare the two images to more accurately identify the portion of the brain associated with the essential tremor motion and can therefore more accurately target this portion of the brain with electrical stimulation. In still further embodiments, (as described above), some or all of the foregoing method portions can be executed automatically by a computer and without generating a visual image.

Referring now to FIG. 7B, a method 700b in accordance with another embodiment of the invention includes directing the collection of first information corresponding to a level of neural activity in the patient's brain while the patient performs a muscle action (method portion 720). In method portion 722, the patient's motor nerves are affected by introducing a drug into the patient's body. The method 700b further includes directing the collection of second information corresponding to a level of neural activity in the patient's brain while the patient performs the muscle action and while the patient is under the influence of the drug (method portion 724). In method portion 726, the patient's essential tremor motion is at least reduced by applying an electrical stimulation at least proximate to a stimulation site, with a location of the stimulation site being based at least in part on a comparison of the first information with the second information. For example, it has been observed that a patient normally subject to essential tremor motion experiences a reduction in essential tremor motion when under the influence of alcohol or other drugs such as propanolol, mysoline, primidone, benzodiazepine or botulinum toxin A. A practitioner can compare neural information associated with muscle action before and after the influence of the drug to more readily determine the location of the patient's brain responsible for the essential tremor motion alone. Accordingly, the practitioner can more accurately target electrical stimulation to this location.

In any of the embodiments described above with reference to FIGS. 1A–7B, the patient can receive drug therapy in conjunction with the electrical stimulation. For example, in a particular embodiment, the drug is administered to the patient so as to be active in the patient's system during electrical stimulation treatment. In a particular aspect of this embodiment, the drug can include alcohol, propanolol, mysoline, primidone, benzodiazepine or botulinum toxin A. In other embodiments, the drug can have other constituents.

From the foregoing, it will be appreciated that specific embodiments of the invention have been described herein for purposes of illustration, but that various modifications may be made without deviating from the spirit and scope of the invention. For example, the leads of the electrode arrays may be coupled to an external pulse generator instead of an implanted pulse generator. Methods and systems in accordance with other embodiments of the invention are included in pending U.S. Provisional Application No. 60/432,073, entitled "System and Method for Treating Parkinson's Disease and other Movement Disorders," filed Dec. 9, 2002 and pending U.S. application Ser. No. 10/317,002, entitled "Systems and Methods for Enhancing or Optimizing Neural Stimulation Therapy for Treating Symptoms of Parkinson's Disease and/or Other Movement Disorders," filed Dec. 10, 2002, both incorporated herein by reference. Accordingly, the invention is not limited except as by the appended claims.

We claim:

1. A method for treating essential tremor, comprising:
   directing a patient to perform a muscle action;
   directing information to be collected, the information corresponding to a level of neural activity in the patient's brain while the patient performs the muscle action; and
   eliminating an essential tremor motion of the patient by applying an electrical stimulation at least proximate to a stimulation site, the location of the stimulation site being based at least in part on the information.

2. A method for treating essential tremor, comprising:
   directing a patient to perform a muscle action;
   directing a computer-based routine to collect information corresponding to a level of neural activity in the patient's brain while the patient performs the muscle action; and
   at least reducing an essential tremor motion of the patient by applying an electrical stimulation at least proximate to a stimulation site, the location of the stimulation site being based at least in part on the information.

3. A method for treating essential tremor, comprising:
   directing a patient to perform a muscle action;
   directing information to be collected on blood oxygen levels in the brain, the information corresponding to a level of neural activity in the patient's brain while the patient performs the muscle action; and
   at least reducing an essential tremor motion of the patient by applying an electrical stimulation at least proximate to a stimulation site, the location of the stimulation site being based at least in part on the information.

4. A method for treating essential tremor, comprising:
   directing a patient to perform a muscle action;
   directing information to be collected, the information corresponding to a level of neural activity in the patient's brain while the patient performs the muscle action;
   locating a stimulation site based at least in part on the information and positioned relative to an anatomical feature of the patient; and
   at least reducing an essential tremor motion of the patient by applying an electrical stimulation at least proximate to the stimulation site.

5. A method for treating essential tremor, comprising:
   directing a patient to perform a muscle action;
   directing information to be collected, the information corresponding to a level of neural activity in the patient's brain while the patient performs the muscle action;
   locating a stimulation site based at least in part on the information relative to a fiducial having a fixed location relative to the patient's skull; and
   at least reducing an essential tremor motion of the patient by applying an electrical stimulation at least proximate to the stimulation site.

6. A method for treating essential tremor, comprising:
   directing a patient to perform a muscle action a first time;
   directing first information to be collected, the first information corresponding to a level of neural activity in the patient's brain while the patient performs the muscle action the first time;
   affecting the patient's motor nerves by introducing a drug into the patient's body;
   directing second information to be collected while the patient performs the muscle action a second time and while the patient is under the influence of the drug;
   directing a comparison of the first information with the second information to identify a stimulation site of the brain; and
   at least reducing an essential tremor motion of the patient by applying an electrical stimulation at least proximate to the stimulation site.

7. A method for treating essential tremor, comprising:
   directing a patient to perform a muscle action;
   directing information to be collected, the information corresponding to a level of neural activity in the patient's brain while the patient performs the muscle action; and
   at least reducing an essential tremor motion of the patient by administering drugs to the patient and applying an electrical stimulation at least proximate to a stimulation site, the location of the stimulation site being based at least in part on the information.

8. A method for treating essential tremor, comprising:
   directing a patient to perform a muscle action;
   directing information to be collected, the information corresponding to a level of neural activity in the patient's brain while the patient performs the muscle action; and
   at least reducing an essential tremor motion of the patient by applying an electrical stimulation at least proximate to a stimulation site, the location of the stimulation site being based at least in part on the information, the electrical stimulation including a varying electrical stimulation signal having an electrical potential of from about 0.25 volts to about 5.0 volts.

9. A method for treating essential tremor, comprising:
   directing a patient to perform a muscle action that includes maintaining a muscle in a particular position;
   directing information to be collected, the information corresponding to a level of neural activity in the patient's brain while the patient performs the muscle action; and
   at least reducing an essential tremor motion of the patient by applying an electrical stimulation at least proximate to a stimulation site, the location of the stimulation site being based at least in part on the information.

10. A method for treating essential tremor, comprising:
    obtaining first information corresponding to a level of neural activity in the patient's brain while the patient does not perform a muscle action;
    directing a patient to perform the muscle action;
    directing second information to be collected, the second information corresponding to a level of neural activity in the patient's brain while the patient performs the muscle action; and at least reducing an essential tremor motion of the patient by applying an electrical stimulation at least proximate to a stimulation site, the location of the stimulation site being based at least in part on a comparison of the second information with the first information.

11. A method for treating essential tremor, comprising:
directing the patient to undergo a plurality of muscle actions;
selecting from the plurality of muscle actions a muscle action that produces a selected level of essential tremor motion;
directing a patient to perform the muscle action to produce the selected level of essential tremor motion;
directing information to be collected, the information corresponding to a level of neural activity in the patient's brain while the patient performs the muscle action; and
at least reducing an essential tremor motion of the patient by applying an electrical stimulation at least proximate to a stimulation site, the location of the stimulation site being based at least in part on the information.

12. A method for treating essential tremor, comprising:
identifying a muscle action subject to essential tremor;
monitoring a first image of the patient's brain function while the patient is not performing the muscle action;
monitoring a second image of the patient's brain function while the patient performs the muscle action;
comparing the first and second images to identify a stimulation site of the brain;
placing at least one electrode at least proximate to the stimulation site;
at least reducing the patient's essential tremor motion by applying an electrical stimulation at least proximate to the stimulation site.

13. The method of claim 12 wherein comparing the first and second images includes comparing a first image having visual characteristic with a first value at least proximate to the stimulation site with a second image having the visual characteristic with a second value different than the first value at least proximate to the stimulation site.

14. The method of claim 12 wherein comparing the first and second images includes comparing a first image having a first baseline region and a first activity region corresponding to increased brain activity relative to the first baseline region, with a second image having a second baseline region and a second region corresponding to increased brain activity relative to the second baseline region, a location of the second activity region being different than a location of the first activity region.

15. The method of claim 12 wherein comparing the first and second images includes comparing a first image having a first baseline region and a first activity region corresponding to increased brain activity relative to the first baseline region, with a second image having a second baseline region and a second activity region corresponding to increased brain activity relative to the second baseline region, with a brain activity level of the second activity region being different than a brain activity level of the first activity region.

16. The method of claim 12 wherein identifying a stimulation site includes determining a region of the patient's brain that corresponds to a portion of the image that changes at least one characteristic as the patient performs the muscle action.

17. The method of claim 12 wherein monitoring the first image includes monitoring a first functional MRI image, and wherein monitoring the second image includes monitoring a second functional MRI image.

18. The method of claim 12 wherein comparing the first and second images includes:
determining a first region of a first hemisphere of the patient's brain corresponding to a portion of the image that changes at least one characteristic as the patient performs the muscle action; and
determining the stimulation location to include a second region of a second hemisphere of the patient's brain, the second region corresponding functionally to the first region.

19. A method for treating essential tremor, comprising:
directing a patient to perform a muscle action;
while the patient performs the muscle action, directing a collection of information corresponding to a level of neural activity in the patient's brain;
directing a comparison of a first portion of the information corresponding to a level of neural activity at the left hemisphere of the patient's brain with a second portion of the information corresponding to a level of neural activity at the right hemisphere of the patient's brain; and
at least reducing an essential tremor motion of the patient by applying an electrical stimulation at least proximate to a stimulation site, with a location of the stimulation site being based at least in part on the comparison of the first and second portions of the information.

20. The method of claim 19 wherein at least reducing an essential tremor motion includes eliminating the essential tremor motion.

21. The method of claim 19 wherein directing information to be collected includes directing a computer-based routine to collect the information.

22. The method of claim 19, further comprising directing the formation of an image of at least a portion of the patients brain, with at least a portion of the image having features representative of the information.

23. The method of claim 19, further comprising implanting at least one electrode at least proximate to the stimulation site, and wherein applying an electrical stimulation includes applying an electrical signal to the at least one electrode.

24. The method of claim 19 wherein applying an electrical stimulation includes applying a varying electrical stimulation signal having a frequency of from about 5 Hz to about 200 Hz.

25. The method of claim 19 wherein applying an electrical stimulation includes applying a varying electrical stimulation signal having an electrical potential of from about 0.25 volts to about 5.0 volts.

26. The method of claim 19 wherein directing the patient to perform a muscle action includes directing the patient to move the muscle.

27. A method for treating essential tremor, comprising:
directing a patient to perform an action with a first muscle on a first side of the patient's body, the first muscle being controlled by a second hemisphere of the patient's brain;
while the patient performs the action with the first muscle, directing a collection of first information corresponding to a level of neural activity in the patient's brain;
directing the patient to perform an action with a second muscle on a second side of the patient's body, the second muscle mirroring the first muscle and being controlled by a first hemisphere of the patient's brain;

while the patient perform an action with the second muscle, directing a collection of second information corresponding to a level of neural activity in the patient's brain; and at least reducing an essential tremor motion of the patient by applying an electrical stimulation at least proximate to a stimulation site, with a location of the stimulation site being based at least in part on a comparison of the first information with the second information.

28. The method of claim 27 wherein at least reducing an essential tremor motion includes eliminating the essential tremor motion.

29. The method of claim 27 wherein directing information to be collected includes directing a computer-based routine to collect the information.

30. The method of claim 27, further comprising directing the formation of an image of at least a portion of the patient's brain, with at least a portion of the image having features representative of the information.

31. The method of claim 27, further comprising implanting at least one electrode at least proximate to the stimulation site, and wherein applying an electrical stimulation includes applying an electrical signal to the at least one electrode.

32. The method of claim 27 wherein applying an electrical stimulation includes applying a varying electrical stimulation signal having a frequency of from about 5 Hz to about 200 Hz.

33. The method of claim 27 wherein applying an electrical stimulation includes applying a varying electrical stimulation signal having an electrical potential of from about 0.25 volts to about 5.0 volts.

34. The method of claim 27 wherein directing the patient to perform a muscle action includes directing the patient to move the muscle.

35. A method for treating essential tremor, comprising:
directing a collection of first information corresponding to a level of neural activity in the patient's brain while the patient performs a muscle action;
affecting the patient's motor nerves by introducing a drug into the patient's body;
directing a collection of second information corresponding to a level of neural activity in the patient's brain while the patient performs the muscle action and while the patient is under the influence of the drug; and
at least reducing the patient's essential tremor motion by applying an electrical stimulation at least proximate to a stimulation site, with a location of the stimulation site being based at least in part on the comparison of the first information with the second information.

36. The method of claim 35 wherein introducing a drug includes introducing ethyl alcohol.

37. The method of claim 35 wherein at least reducing an essential tremor motion includes eliminating the essential tremor motion.

38. The method of claim 35 wherein directing information to be collected includes directing a computer-based routine to collect the information.

39. The method of claim 35, further comprising directing the formation of an image of at least a portion of the patient's brain, with at least a portion of the image having features representative of the information.

40. The method of claim 35, further comprising implanting at least one electrode at least proximate to the stimulation site, and wherein applying an electrical stimulation includes applying an electrical signal to the at least one electrode.

41. The method of claim 35 wherein applying an electrical stimulation includes applying a varying electrical stimulation signal having a frequency of from about 5 Hz to about 200 Hz.

42. The method of claim 35 wherein applying an electrical stimulation includes applying a varying electrical stimulation signal having an electrical potential of from about 0.25 volts to about 5.0 volts.

43. The method of claim 35 wherein directing the patient to perform a muscle action includes directing the patient to move the muscle.

* * * * *

UNITED STATES PATENT AND TRADEMARK OFFICE
CERTIFICATE OF CORRECTION

| | |
|---|---|
| PATENT NO. | : 6,959,215 B2 |
| APPLICATION NO. | : 10/622898 |
| DATED | : October 25, 2005 |
| INVENTOR(S) | : Bradford Evan Gliner et al. |

It is certified that error appears in the above-identified patent and that said Letters Patent is hereby corrected as shown below:

Title Page under Abstract Col. 2 line 38
"43 Claims, 9 Drawing Sheets" should be --48 Claims, 9 Drawing Sheets"--;

The following Amendments to the Claims were made in an Amendment filed March 22, 2005, and allowed by the Examiner in the Notice of Allowance dated June 2, 2005:

Please cancel claim 1 and add new claims 51-56, as amended:

1.  (Cancelled) → Col. 11 lines 15-20
   Col. 16 line 41-

51.  (New)  The method of claim 15 wherein the information includes second information and wherein applying an electrical stimulation at least proximate to a stimulation site includes applying an electrical stimulation to a stimulation site having a location based on a comparison of the second information with first information, the first information corresponding to a level of neural activity in the patient's brain while the patient does not perform the muscle action.

52.  (New)  The method of claim 15 wherein applying an electrical stimulation includes applying a varying electrical stimulation signal having a frequency of from about 5 Hz to about 200 Hz.

53.  (New)  The method of claim 15 wherein applying an electrical stimulation includes applying a varying electrical stimulation signal having an electrical potential of from about 0.25 volts to about 5.0 volts.

54.  (New)  The method of claim 17 wherein the information includes second information and wherein applying an electrical stimulation at least proximate to a stimulation site includes applying an electrical stimulation to a stimulation site having a location based on a comparison of the second information with first information, the first information corresponding to a level of neural activity in the patient's brain while the patient does not perform the muscle action.

55.  (New)  The method of claim 17 wherein applying an electrical stimulation includes applying a varying electrical stimulation signal having a frequency of from about 5 Hz to about 200 Hz.

UNITED STATES PATENT AND TRADEMARK OFFICE
CERTIFICATE OF CORRECTION

PATENT NO.       : 6,959,215 B2
APPLICATION NO.  : 10/622898
DATED            : October 25, 2005
INVENTOR(S)      : Bradford Evan Gliner et al.

It is certified that error appears in the above-identified patent and that said Letters Patent is hereby corrected as shown below:

56.  (New)  The method of claim 17 wherein applying an electrical stimulation includes applying a varying electrical stimulation signal having an electrical potential of from about 0.25 volts to about 5.0 volts.

Signed and Sealed this

Twenty-second Day of August, 2006

JON W. DUDAS
*Director of the United States Patent and Trademark Office*